United States Patent [19]

Kenkare et al.

[11] 4,088,751

[45] May 9, 1978

[54] SELF-HEATING COSMETIC

[75] Inventors: Divaker B. Kenkare, South Plainfield; Frederick W. Gray, Summit; Durland K. Shumway, Piscataway, all of N.J.

[73] Assignee: Colgate-Palmolive Company, New York, N.Y.

[21] Appl. No.: 628,451

[22] Filed: Nov. 3, 1975

Related U.S. Application Data

[63] Continuation of Ser. No. 242,191, Apr. 7, 1972, abandoned, which is a continuation-in-part of Ser. No. 20,384, Mar. 17, 1970, abandoned.

[51] Int. Cl.$^2$ .............................................. A61K 7/06
[52] U.S. Cl. ....................................... 424/47; 8/161; 252/DIG. 13; 252/90; 424/59; 424/62; 424/65; 424/70; 424/73; 424/168; 424/358
[58] Field of Search ..................................... 424/47, 73

[56] References Cited

U.S. PATENT DOCUMENTS

| | | | |
|---|---|---|---|
| 3,326,416 | 6/1967 | Hayes ...................................... | 424/73 |
| 3,341,418 | 9/1967 | Moses et al. ........................... | 424/73 |
| 3,585,982 | 6/1971 | Hollinshead ........................... | 126/263 |

OTHER PUBLICATIONS

Coke et al., Chem. Abs., 1947, vol. 41, p. 2003.

*Primary Examiner*—Dale R. Ore
*Attorney, Agent, or Firm*—Herbert S. Sylvester; Murray M. Grill; Norman Blumenkopf

[57] ABSTRACT

A packaged self-heating cosmetic, such as a shaving cream, hand lotion, depilatory, facial, or a shampoo, including separate exothermically reactive reductant material, such as 2-thio-4-oxyprimidine or thiohydantoin or derivatives thereof, and an oxidant, which reacts with the reductant, generating heat. Means are provided for dispensing the packaged reductant and oxidant from separate zones and bringing them into contact with each other so that they react and heat a pressurized shaving cream or other cosmetic product whose constituents the exothermic reaction mixture contacts. The reducing agent employed is preferably 2-thio-4-oxyprimidine or its tautomer, 2-mercapto-4-hydroxypyrimidine, or alkyl-substituted derivative thereof, and the oxidizing agent is preferably aqueous hydrogen peroxide.

15 Claims, No Drawings

SELF-HEATING COSMETIC

This is a continuation, of application Ser. No. 242,191 filed Apr. 7, 1972, which was in turn a continuation-in-part of application Ser. No. 20,384, filed Mar. 17, 1970, both now abandoned.

Various cosmetic preparations, such as shaving creams, hand lotions, body lotions, facial preparations, including masks, depilatories, hair dyes and shampoos for the hair, have been found to be more effective and often more pleasant to use when applied warm or hot, rather than at room temperature. Because of recent findings that self-heating preparations could be produced and subsequently dispensed conveniently from two-compartment "aerosol" dispensers, self-heating cosmetic preparations have been made and have enjoyed commercial successes. Perhaps the area of most interest at the present time is that of self-heating shaving creams, which include chemical reactants, such as oxidants and reductants, which react exothermically upon mixing on dispensing, to produce heat. The heat generated warms the shaving lather or other cosmetic material, making the action thereof faster and more effective. Preferably, such shaving preparations and other types of cosmetics will be dispensed in a foam or expanded form, with the foaming agent usually being a pressurized gas or low-boiling liquid, such as a chloro-, fluoro-, or chlorofluoro-lower hydrocarbon which provides both the gaseous portion of the bubble structure and the driving force for dispensing the reactants from a container upon opening of a dispensing valve.

Although various chemical reactions, including oxidation-reduction, neutralization, hydration, hydrolysis and metathesis, are capable of generating heat sufficient to warm a cosmetic being dispensed, care must be taken to make certain that the reactants and byproducts thereof are cosmetically acceptable and are non-reactive with the other cosmetic constituents. For example, many sulfur-containing materials are malodorous or develop a malodor, thereby destroying the aesthetic appeal of a cosmetic, although they may be functionally effective. Other materials interact with ingredients of the cosmetic with which they are brought into contact and adversely affect the functions of such materials. Still others are toxic or irritating. Finally, some reactant systems, although they are compatible with the cosmetics and are otherwise acceptable, have to be employed in such proportions to generate sufficient heat that the use thereof is not practicable in commercial products. Even if the oxidant and the reductant are acceptable, available and of low cost, if unduly large quantities are required to generate heat, the exothermic reactants are in effect replacing cosmetic materials, thereby adding weight and volume to the product without any corresponding useful cosmetic action. If this displacement is of a minor proportion of cosmetic, considering the advantages gained by the generation of heat, it may be tolerated, but when excessive, other exothermic material must be found. In some cases, only one of the reactants might be required in a proportion more than that normally used in 2-compartment dispensers. Yet, even if only the oxidant is required in excess, it can make the use of the system impractical where the compartment normally provided for the oxidant is smaller than needed in order to generate sufficient heat to raise the temperature of the cosmetic to that which is desired.

It has been found that the use of 2-thio-4-oxypyrimidine or various derivatives or analogues thereof as a reductant, together with an oxidizing agent, such as hydrogen peroxide, results in an exothermic system which is compatible with a wide variety of cosmetic compositions, which occupies a reasonable volume of a cosmetic dispenser, which is not malodorous, which is compatible with cosmetic constituents, which is non-toxic and which is not dermatologically irritating. Such results are obtained at reasonable expense. In accordance with the present invention there is provided a packaged self-heating cosmetic preparation, such as a shaving cream, which includes separate, exothermically reactive 2-thio-4-oxypyrimidine, an analogous thiohydantoin or a substituted derivative thereof, as a reductant, and an oxidant, such as an aqueous solution of hydrogen peroxide, which react, with the generation of heat. The product of the reaction and the reactants are compatible with other cosmetic ingredients and the product and the reductant are essentially organic, which is advantageous for compatibility with perfumes, vegetable materials, soaps, foaming agents and other organic bases for cosmetics. Such products are often superior in heat-generating properties. Furthermore, by utilizing appropriate substituents, the properties of the thiopyrimidines and thiohydantoins may be modified to make them essentially more like the other cosmetic ingredients in nature, whereby the may aid in solubilizing such materials. Although the mentioned reductants and oxidants will react and the presence of a catalyst is not required to allow them to generate heat, it is much preferred if a catalyst is present at the time of contact of the oxidant and reductant, so as to speed the reaction and allow a more rapid generation of heat in the cosmetic. In some products, however, gradual and slower heating may be desired, in which cases the catalyst may be omitted or decreased in quantity.

Interaction of the oxidants and reductants of this invention is effected by simultaneous discharge thereof from separate sources or compartments of a plural compartment container or other suitable package or packages in which the oxidant and reductant compositions are stored separately. Upon such discharge or shortly thereafter, at the intended time of use of the cosmetic, the final cosmetic preparation is constituted and the required heat is generated. At the time of contact there are present the other cosmetic or shaving cream constituents and the cosmetic is heated to a satisfactory high temperature, preferably as it is dispensed but sometimes shortly thereafter. For example, within a period of 5 to 30 seconds appreciable warmth is usually noted. Sometimes, the temperature of the cosmetic may not reach a maximum until 20 to 60 seconds after initial discharge of the products and contact of the oxidant with the reductant. At present, many preferred formulations of this invention reach a maximum temperature within about 5 to 20 seconds. Such a relatively gradual heating rate is preferred by many consumers. Of course, instead of using a single container having a plurality of compartments, a combination of containers or sources of oxidant, reductant and cosmetic materials may be employed. Thus, all these three types of materials or suitable mixtures thereof may be brought together at approximately the same time, when dispensed.

In preferred embodiments of the invention the reductant employed is 2-thio-4-oxypyrimidine, preferably in a composition with other cosmetic or shaving cream constituents, and the oxidant is an aqueous solution of hydrogen peroxide kept separate from the other cosmetic materials until the time of dispensing. However, as was mentioned previously, substituted derivatives of the 2-thio-4-oxypyrimidine or analogues thereof are also useful and can be preferable in particular circumstances. It is also within the invention to employ mixtures of such reducing agents.

The plural compartment dispensers used are well known in the art and are commercially available. In such dispensing containers, a single vessel usually includes a main compartment of a generally cylindrical shape which contains liquefied gas and other ingredients, plus a small compartment or sac which is collapsible under the pressure of the liquefied gas, as the contents are dispensed and the volume of liquid material in the vessel is diminished. A valve communicates with the contents of the compartments by means of dip tubes or suitable connections and allows simultaneous dispensing of the contents, when the valve is opened. Such a valve or plural valves, as the case may be, are actuatable by movement of a dispensing member, which may be a spout. Usually, the contents of the compartment are passed through the spout member, wherein they are mixed, and are then discharged from the spout is heated form, ready for use. A suitable dispenser is illustrated in U.S. Pat. No. 3,325,056, wherein the mixing of the reactive components occurs internally in the valve. However, it is preferred for such mixing to be effected externally of the container, preferably in the spout member. In addition to the integral dispensing container, one may also employ combinations of dispensers, each of which contains one of the reactive materials, often in combination with other cosmetic constituents. Such a combination may be like that illustrated in U.S. Pat. No. 3,451,593.

The proportions of oxidant and reductant used will normally be about those which are stoichiometric. However, in some circumstances, where it is desired to force the reaction by employing an excess of one or the other of the reactants or where it is useful for the final composition to be of a reducing or oxidizing character, an excess, such as 25 to 50% of either oxidant or reductant may be employed. Generally, such excess will be no more than 10% of the stoichiometric quantity and preferably, in the usual case, approximately stoichiometric proportions will be used. Such proportions are with respect to reactions for effecting either the complete oxidation of the reductant or an intermediate partial oxidation thereof to a specific intermediate compound. Thus, the mole ratio of hydrogen peroxide to 2-thio-4-oxypyrimidine will normally be from 1 to 8, depending on the extent to which it is desired to carry the oxidation.

The temperature to which the cosmetic will be raised upon dispensing is usually controlled by valve design, viscosities of the oxidant and reductant compositions, the specific identities of the oxidant and the reductant employed and their proportions. Usually such temperature will be from 100° to 160° F., preferably from 120° to 150° F. and most preferably from 130° to 145° F. Thus, the increase in the temperature of the cosmetic over room temperature will usually be from 30° to 100° F. Most often it will be about 60° to 80° F. Although heating to such temperature is effected substantially all of the time, nevertheless, the use of the present invention to dispense cosmetic materials at other temperatures is also contemplated, when preferable.

The 2-thio-4-oxypyrimidine, derivatives and analogues may be characterized as being of either of the following formulas:

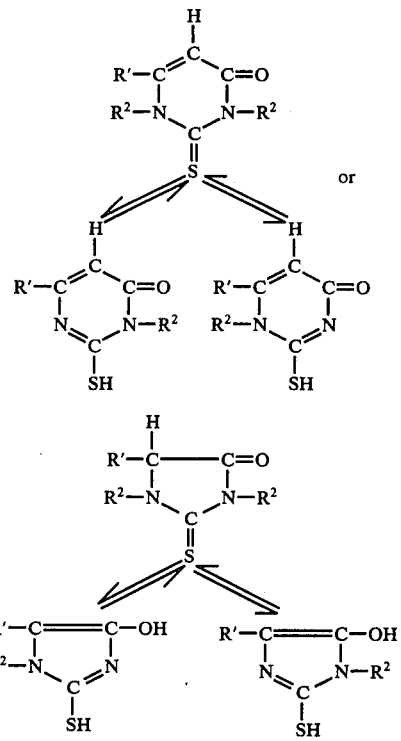

wherein $R^1$ is hydrogen, lower alkyl, phenyl, lower hydroxyalkyl, lower alkoxy, poly-lower alkoxy, lower alkoxy-lower alkyl, poly-lower alkoxy-lower alkyl or lower alkanoyloxy and $R^2$ is hydrogen, lower alkyl, phenyl, lower hydroxyalkyl, lower alkoxy-lower alkyl, poly-lower alkoxy-lower alkyl or lower alkanoyl, with the provision that at least one of the $R^2$'s usually is hydrogen. The lower alkyls and alkoxy groups are usually of 1 to 6 carbon atoms and preferably are of 1 to 3 carbon atoms and the number of alkoxies in the polyalkoxy group is usually from 2 to 10. Ordinarily, the hydroxyalkyls are monohydroxyalkyls, although in some instances it may be desirable to have two or three hydroxyls per alkyl group. If a single hydroxyl is present, it is ordinarily terminally joined to the alkyl. Of course equivalent compounds may be employed wherein non-interfering substituents are present on the recited radicals. Such substituents may include chlorine, other halogens, nitro, amino, alkyl and phenyl, when useful under the particular conditions.

Although, for tautomeric configurations, it is desirable that the 5-carbon and either the 1- or 3-nitrogen of the thiooxypyrimidine should be unsubstituted (containing only hydrogen, except for ring joinders), in some circumstances it may be acceptable to have both of the $R^2$ substituents different from hydrogen. Thus, it has been found that sometimes even more heat is generated when two $R^2$'s are present per thiooxypyrimidine moiety. Of course, it is usually preferable for the tautomeric configuration to be encouraged, wherein at least one $R^2$ is a hydrogen. When both are substituents, these substituents may be the same or different. A similar rule applies with respect to the thiohydantoin compounds which are analogous to the thiooxypyrimidines. Nevertheless, in some instances it may also be desirable in such cases to have $R^2$'s on each of the nitrogens of the thiohydantoin. In certain applications the oxygens of the thiooxypyrimidine and the thiohydantoin may be replaced by hydrogen atoms or a single hydrogen and an $R^1$ substituent. Although such compounds are useful in reactions with oxidizing agents to generate heat, they are not considered to be the preferred exothermic reactants of the present invention.

Specific examples of reductants considered to be useful in the practice of this invention are compounds of the formulas given: 2-thio-4-oxypyrimidine; 1-methyl-2-thio-4-oxypyrimidine; 1-ethyl-2-thio-4-oxypyrimidine; 1-n-hexyl-2-thio-4-oxypyrimidine; 2-thio-3-methyl-4-oxypyrimidine; 2-thio-3-butyl-4-oxypyrimidine; 2-thio-3-n-amyl-4-oxypyrimidine; 1-phenyl-2-thio-4-oxypyrimidine; 2-thio-3-phenyl-4-oxypyrimidine; 1-(2-hydroxyethyl)-2-thio-4-oxypyrimidine; 1-(5-hydroxyethyl)-2-thio-4-oxypyrimidine; 2-thio-3-hydroxymethyl-4-oxypyrimidine; 2-thio-3-(5-hydroxyamyl)-4-oxypyrimidine; 1-t-butyl-2-thio-4-oxypyrimidine; 1-ethoxyethyl-2-thio-4-oxypyrimidine; 2-thio-3-butoxymethyl-4-oxypyrimidine; 1-tri (n-propoxy)propyl-2-thio-4-oxypyrimidine; 2-thio-3-pentaethoxymethyl-4-oxypyrimidine; 1-acetyl-2-thio-4-oxypyrimidine; 2-thio-3-propionyl-4-oxypyrimidine; 2-thio-6-methyl-4-oxypyrimidine; 2-thio-6-amyl-4-oxypyrimidine; 2-thio-6-phenyl-4-oxypyrimidine; 2-thio-6-hydroxy-n-propyl-4-oxypyrimidine; 2-thio-6-(5-hydroxyhexyl)-4-oxypyrimidine; 2-thio-6-methoxy-4-oxypyrimidine; 2-thio-6-t-butoxy-4-oxypyrimidine; 2-thio-6-pentaethoxy-4-oxypyrimidine; 2-thio-6-dipropoxy-4-oxypyrimidine; 2-thio-6-methoxyethyl-4-oxypyrimidine; 2-thio-6-amyloxybutyl-4-oxypyrimidine; 2-thio-6-triethoxyethyl-4-oxypyrimidine; 2-thio-6-butyroxy-4-oxypyrimidine; 2-thio-6-acetoxy-4-oxypyrimidine; 1-phenyl-2-thio-6-methyl-4-oxypyrimidine; 2-thio-3-n-hexyl-6-pentaethoxy-4-oxypyrimidine; 1-butoxybutyl-2-thio-6-acetyloxy-4-oxypyrimidine; 2-thio-3-triethoxyethyl-6-phenyl-4-oxypyrimidine; thiohydantoin; 1-methyl-thiohydantoin; 1-butyl-thiohydantoin; 3-ethyl-thio-hydantoin; 1-phenyl-thiohydantoin; 3-phenyl-thio-hydantoin; 1-hydroxyethyl-thiohydantoin; 3-(4-hydroxy-n-butyl)-thiohydantoin; 1-ethoxymethyl-thiohydantoin; 3-(n-amyloxy-n-propyl)-thiohydantoin; 1-triethoxyethyl-thiohydantoin; 3-decapropoxypropyl-thiohydantoin; 1-acetyl-thiohydantoin; 3-pentanoyl-thiohydantoin; 5-ethyl-thio-hydantoin; 5-phenyl-thiohydantoin; 5-(3-hydroxy-n-propyl)-thio-hydantoin; 5-n-butoxy-thiohydantoin; 5-(hexapropoxy)-thiohydantoin; 5-ethoxypropyl-thiohydantoin; 5-(triethoxy)methyl-thio-hydantoin; 5-propionoxy-thiohydantoin; 1-isopropyl-5-acetoxy-thiohydantoin; 1-hydroxyethyl-5-phenyl-thiohydantoin; 3-n-butoxy-5-triethoxyethyl-thiohydantoin; and 3-propanoyl-5-(heptaethoxy)ethyl-thiohydantoin.

Although the above extensive listing of compounds considered to be representative to those which could be utilized as the reductants in this invention includes many such materials within the scope of the class of such useful reductants, even though some may be difficult to manufacture, it is not exhaustive and it will be clear that other feasible compounds within the descriptions given in this specification may also be employable. Manufacturing methods may be modified accordingly. For example, other compounds might be made within substituents described in the foregoing examples are exchanged with hydrogen or other substituents. Thus, $R^2$ may replace free hydrogens on the rings other than the $R^1$ hydrogen and the $R^2$'s used may be those illustrated in the named compounds. Also, modifications of these materials, in accordance with the descriptions thereof herein are contemplated. Of course, the tautomers are also intended to be included.

Heat is rapidly and efficiently generated when the thiooxypyrimidines, the thiohydantoins and other compounds useful as reductants in the present invention or their described derivatives or tautomers, all of which, for convenience, will be referred to generally hereinafter as thiooxypyrimidines, are reacted with a suitable oxidizing agent, such as hydrogen peroxide or other such compound which is acceptable in the cosmetic compositions. In addition to good generation of heat, it has been found that products of the reactions, which may include the corresponding sulfones, sulfoxides, oxides, sulfates, etc., are compatible with the usual cosmetic or shaving cream ingredients. By selection of the types of substituents on the carbon or nitrogen atoms of the thiooxypyrimidines, the properties of the compounds, in relation to the medium in which they are incorporated and in relationship to other cosmetic ingredients may be varied. Thus, by substituting carbon or nitrogen atoms of the present reductants with hydroxyalkyl, alkoxy or polyalkoxy groups, wherein the alkoxy and alkyl are of about 1 to 4 carbon atoms, water solubility of the compounds may be increased, thereby increasing its compatibility with hydrophilic cosmetic ingredients. Similarly, by substituting alkyl groups, especially those of a number of carbon atoms from 5 to 8 or more, lipophilic character may be increased without making the product incompatible with hydrophilic components of the compositions. Thus, the present compounds lend themselves to use in a wide variety of cosmetic formulations, in which they may be readily solubilized and in which they may contribute to the solubilization of other components. In such a way, compatibilities with the other ingredients of the cosmetics can be increased. By utilizing mixtures of various thiooxypyrimidines, balanced characteristics of the reductants may be obtained in the finished product.

Although the compounds utilized in this invention contain sulfur, they are useful in cosmetic compositions because the products made by oxidation are not of objectionable odor and are compatible with cosmetic ingredients. Thus, somewhat unexpectedly, fairly delicate perfumes may still be employed with the present cosmetic products and are not destroyed or excessively overpowered by the presence of sulfur-containing compounds or reaction products.

The oxidizing agent which is reacted with the thiooxypyrimidine to generate heat therefrom may be any suitable such compound which converts the sulfur of the thiooxypyrimidine to a more oxidized form thereof, such as the sulfone, sulfoxide or sulfate and oxide. In addition, such an oxidizing agent also might react with carbon or hydrogen atoms of the thiooxypyrimidine to generate additional heat by converting them to oxides, per-oxides, hydroxyls or other reacted forms. Although a great variety of organic and inorganic oxidizing agents is known and may be employed for such reaction, it is preferred to use per-compounds. Of these, the inorganic per-compounds are preferred, especially those which are converted to innocuous or useful by-products. Of course, the best of these will often be hydrogen peroxide, which is preferably utilized as stabilized aqueous solution. However, other per-compounds, such as various metal peroxides and per-salts, including sodium peroxide, sodium perborate, potassium percarbonate and sodium persulfate are also useful.

Organic peroxides, such as urea peroxide and various equivalents thereof may also be employed. Such percompounds are preferably used as alkali metal, alkaline earth metal or other metal salts, if not in the form of hydrogen peroxide. In addition, materials which release hydrogen peroxide or useful oxygen are suitable oxidants for the present invention Mixtures of such materials may be employed to adjust properties of the oxidizing agents or to obtain special effects.

The reason that hydrogen peroxide is a preferred oxidizing agent is that the products obtained therefrom are limited to water and oxygen and, when the oxygen is entirely consumed in converting the sulfur to a higher state of oxidation, only water is a byproduct. Since water is a normal and desired constituent of many cosmetic compositions, including shaving creams, and does not add any irritating materials to the product, hydrogen peroxide is highly preferred as an oxidizing agent. Similarly, the water and surface active ingredients of the cosmetic composition, including surface active products of the oxidation-reduction reaction, in combination, help to solubilize cosmetic ingredients and improve surface activity of the final preparation.

The oxidizing agent used is preferably a separate aqueous solution, not in contact with the other cosmetic and reducing agent constituents of the present preparation until the time of dispensing. There are times when the oxidizing agent may be present with some of the cosmetic materials but these are not the usual cases. The concentration of the oxidant in water may be varied widely, depending on the particular preparations involved. However, usually from 3 to 70% of the percompound will be employed. When hydrogen peroxide is used this will be from 5 to 60% and preferably from 8 to 40%, with the most usual concentrations being 9 to 20% of the hydrogen peroxide in aqueous solution. Use of the higher concentrations aids in keeping container size as small as possible or, stated differently, having a maximum amount of cosmetic contained therein, accompanied by maximum freedom in formulation. Of course, present with the hydrogen peroxide solution may be minor proportions of sequestrants, chelating agents and other stabilizers, such as nitrilotriacetic acid or its trisodium salt, ethylene diamine tetraacetic acid or a salt thereof, stannic chloride, silicates or other known compounds useful to stabilize hydrogen peroxide.

The speed of the redox reaction between the peroxide and the thiooxypyrimidine reducing agent is significantly increased by the presence of metal catalysts. Thus, tungstates, molybdates and uranates, and other salts and catalytic materials for such oxidation reactions, which may operate by activating the peroxide, may be used to increase the reaction efficiency of a redox system employing per-compounds, such as hydrogen peroxide, as the oxidant. Usually, the alkali metal or ammonium salts are used, e.g., ammonium molybdate, potassium tungstate, or sodium uranate. Because metals that activate hydrogen peroxide systems might also act to convert the hydrogen peroxide to a less stable form, in following the present invention the catalyst will usually be present in the zone containing the thiooxypyrimidine and will not contact the stabilized peroxide until the thermogenic reaction is to be effected. Although the redox reaction will proceed and heat will be generated without use of a catalyst, for rapid generation of heat, in preferred embodiments of the invention, a metal salt catalyst for the redox reaction will usually be employed. Such catalysts are known as those which activate the decomposition or reaction of hydrogen peroxide.

The components of the cosmetic composition within the present invention are those known to the cosmetic art to impart desired properties for particular cosmetic purpose. Most cosmetics and shaving cream preparations include both hydrophilic and lipophilic components, often together with emulsifying or wetting agents to help convert them to a stable uniform emulsion. For example, in an emulsion the lipophilic phase may include lanolin, mineral oil, stearic acid, petrolatum, animal fats, vegetable and petroleum waxes and emollients. The aqueous or polar phase may contain water glycerol, solvents, buffers, depilatories, bleaches, waving agents, astringents, stabilizers, deodorants, antiperspirants, or other active materials. Soaps or synthetic organic emulsifiers, surface active agents and detergents may also be present in the aqueous phase and assist in maintaining the emulsion form. Of course, some materials are present in both phases, the greater proportion usually being found in that phase in which the material is more soluble. In some cases, solutions may be used instead of emulsions. The material dispensed may be in any of several physical forms, including liquid, paste, gel or foam. Foams may be created by the action of a dissolved pressurized or liquefied gas dispersed throughout the composition. The gas expands the composition as the pressure on it is released, thereby creating the foam. Preferably, for many cosmetic compositions and especially for shaving creams, a stable foam form is employed, although sometimes one which is easily reduced to a liquid may be preferred.

In shaving preparations, the shaving emulsion dispensed from one compartment of a pressurized container comprises a major proportion, up to about 95% of water, usually 50 to 75%, and the rest of the material includes soap or other beard softeners, solvents, solubilizers, emulsifying, wetting and conditioning agents. The soap is preferably a stearic acid soap, made from commercial double- or triple-pressed stearic acid. However, other higher fatty acid soaps, such as those of tallow, coconut oil, corn oil, cottonseed oil, animal greases and other animal fats and vegetable oils may be employed. Usually however, a major proportion of the soap-forming fatty acid of the soap should be of 16 to 18 carbon atoms. The cation of the soap is preferably an alkanolamine, such as triethanolamine, although other tri-, di-, and mono-alkanolamines of 1 to 4 carbon atoms per alkyl group are useful, such as di-isopropanolamine. If desired, alkali metal soaps, such as sodium and potassium soaps may be employed, as may be ammonium and lower alkyl amine soaps. For best results in producing a soap which does not irritate the skin after shaving and which is fluid enough so as to be dispensed entirely from the container, a triethanolamine soap is used. Minor proportions of sodium and potassium soaps are often added to help stabilize the lather. When superfatting effects are desired, the fatty acid employed, from which the soap is made, may be only partly neutralized by the cation of a neutralizing agent, leaving some free fatty acid present to exert its emollient effect upon the skin. Usually, in such cases the free fatty acid will be from 0.5 to 30%, preferably 10 to 25% of the soap content.

Alkylolamides also have a conditioning effect on the hair and skin, in addition to their property of stabilizing foams of cosmetic compositions. Included in the alkylolamide group are dialkylolamides, such as coconut oil fatty acids diisopropanolamide, lauric-myristic diethanolamide, and other alkylolamides wherein the acyl groups are of 12 to 18 carbon atoms, preferably with 50% by weight or more being of 12 to 14 carbon atoms. The alkylol groups are preferably of 1 to 3 carbon atoms each. Although desirable in many cosmetic compositions, often the functions of the alkylolamides may be performed by other ingredients or may be unnecessary, in which cases the alkylolamides may be omitted. Suitable substitutes for them as thickeners for foams are the higher fatty acid monoglyceride sulfonates at concentrations of 0.1 to 1.5%.

Various suitable emulsifying or surface active agents may be important ingredients of the present products. These include the nonionic, anionic and cationic compounds. Of these materials it is preferred to use the nonionics to the exclusion of anionics and cationics, except of the soap, and of the nonionics the most preferable group is that of the higher ethers of lower alkoxylated alkyl phenols and of higher fatty alcohols. These compounds, known commercially as Igepals, a trademark of GAF Corporation, usually have an alkyl group of 6 to 10 carbon atoms on the phenyl ring and the degree of alkoxylation (ethoxylation) is from 1 to 50, preferably of 10 to 40 ethoxy groups per molecule, with the higher fatty alcohol being of 10 to 18 carbon atoms per molecule, usually averaging about 12 carbon atoms. Other nonionic compounds, such as esters of higher fatty acids and ethoxylated alcohols, condensates of different higher ethylene oxide polymers and higher propylene oxide polymers, and esters of ethoxylated fatty acids and sugar alcohols or hexitans are representative of the nonionics that may be included in the present formulation. Among the anionic surface active agents are the higher alkyl sulfates and alkyl sulfonates, the higher alkyl benzene sulfonates, ethoxylated fatty alcohol sulfates, monoglyceride sulfates, higher fatty acid amides, including such as sodium lauroyl sarcoside, phosphates corresponding to the above-mentioned sulfates, and sulfates and sulfonates of the mentioned nonionic compounds, where possible. Among the cationic surface active agents may be mentioned the quaternary ammonium and phosphonium compounds, e.g., trimethyl benzyl ammonium chloride, cetyl trimethyl ammonium bromide and lauryl pyridinium chloride, all of which exert antiseptic, as well as surface activities. Other emulsifying and surface active agents are described in *Cosmetic Science and Technology*, by Edward Sagarin (Interscience Publishers, 1957), particularly at pages 1006-1008, 1060-63, 775 and 776. This text also contains descriptions of other cosmetic materials, such as various active ingredients, solvents, emollients, liquefiable gas propellants, conditioning agents, soaps, fatty materials, etc.

In self-pressurized "aerosol" compositions a liquefied gas, such as lower hydrocarbon or a lower halogenated hydrocarbon, may be employed, to aid in discharging the oxidant and reductant portions of the cosmetic preparation. Especially when the liquefied gas is emulsified into one or both of the portions of the cosmetic, it will assist in generating a foam as the liquefied propellant is converted to minute gas bubbles. If it is desired to avoid using hydrocarbons or halogenated hydrocarbons, they may be replaced with compressed nitrogen, carbon dioxide, the inert gases or other non-liquefied gas, which provides the force to discharge the oxidant material. Among the liquefied gas propellants which may usually be employed are the lower hydrocarbons of 3 to 4 carbon atoms, which include n-butane, isobutane and propane, preferably employed as a mixture of isobutane and propane, preferably 85 to 90 parts isobutane and 10 to 15 parts propane. The halogenated hydrocarbons are preferably those which are at least partially fluorinated, including monochlorotrifluoromethane, dichlorodifluoromethane, trichlorotrifluoroethane, dichlorotetrafluoroethane, monochloropentafluoroethane, trichloromonofluoromethane, tetrachlorodifluoroethane, and similar chlorofluorohydrocarbons, having 1 to 3 carbon atoms per molecule. Of course, mixtures of the halogenated hydrocarbons are also employed, desirably to regulate the pressure developed, solubilizing properties, corrosion prevention, emulsion formation, and so forth. In some instances it may be preferable to utilize completely chlorinated or fluorinated hydrocarbons as propellants or diluents, e.g., methylene chloride, where they are acceptable.

Cosmetic compositions contain adjuvant materials to make the products aesthetically acceptable or specially appealing. Perfumes, dyes, pigments, emollients, solvents, thickeners, solubilizers, humectants, buffers, antiseptics, foaming agents, preservatives and similar materials, generally in minor proportions, usually less than 5% each and preferably less than 2% each and most preferably less than 1% each, with the total thereof being less than 25%, preferably less than 10% and most preferably less than 5% of the compositions, are often employed.

As emollients or solvents it is preferred to employ polyhydric alcohols of 3 to 6 carbon atoms per molecule, having 3 to 6 free hydroxyls per molecule. Exemplary of such compounds are glycerol and sorbitol, although other alcohols such as pentaerythritol, mannitol and other sugar alcohols are also used. Of course, lanolin, and derivatives thereof may also be present.

The proportions of various other constituents of the present compositions are regulated to a large extent by the type of compositions being prepared. Usually for cosmetic compositions there will be present from 2 to 50% of the active cosmetic ingredient, although more or less may also be employed in special cases. There will also usually be employed from 5 to 90% solvent or dispersing medium and from 1 to 50% of surface active agent, which group includes soaps. In some circumstances, as in shaving creams, the active ingredient and the surface active agent may be the same, since one compound serves both functions. In pressurized compositions, there will usually be present from 3 to 90% of liquefied or compressed gas. Of course, the given proportions apply to most cosmetics, but it must be realized that for certain compositions proportions outside the given ranges may also be acceptable, even preferred.

Pressurized shaving creams of this invention preferably contain from 50 to 85% water, more preferably 65 to 80%, 1 to 20% of synthetic organic surface active agent, preferably 2 to 8% thereof, and 5 to 20% soap, preferably 8 to 15% thereof. There may also be present 2 to 20% of humectant, such as glycerine or sorbitol, which may also exert a solvent action in the composition. Of course, when humectant activity is not considered to be needed, such materials may be omitted. In most compositions minor proportions of foaming agent and perfume, both usually within the range of 0.1 to 5% and preferably, from 0.3 to 1%, are also often utilized. In heated shaving creams the soap solution will usually include from 0.5 to 40%, and preferably from 0.8 to 20%, of the thiooxypyrimidine reductant (which term applies also to the various previously mentioned reductants), but the thiooxypyrimidine compound may also be separately dispensed. Together with the thiooxypyrimidine or separately dispensed there will often be present 0.2 to 2%, preferably 0.3 to 1% of molybdate or tungstate catalyst or other suitable catalyst for the reaction in desirable amount. The hydrogen peroxide contained in the separate compartment to avoid premature contact with the reductant will usually be from 1 to 10% of the weight of the soap solution and will be present as an aqueous solution of from 5 to 60% strength. The hydrogen peroxide solution is usually from 10 to 80% of the soap solution weight and is preferably about 20 to 50% thereof.

The pH of shaving preparations is normally regulated to be on the alkaline side and is preferably no higher than 10.5. Thus, it is preferable to employ compositions having a pH of 7 to 10, and most preferably 7.7 to 8.7, although those of pH from 5 to 11 may also be used, when desired for particular types of applications. The pH may be regulated by use of compatible buffers, such as acid-base, salt-base and acid-salt mixtures, e.g., including borates, phosphates, carbonates, sulfates or silicates, or other acceptable inorganic or organic salts, including salts of alkylolamines. The soap or soaps present in the shaving compositions and the sulfoxides, sulfones or other compounds produced in the thermogenic reaction may exert buffering effects and the soaps may be the primary buffers present.

The cosmetic preparations of this invention are made by simple methods known to the art. The various constituents of the cosmetic portions of the preparations themselves may be combined in the normal manner and then, depending on the nature of the cosmetic, may be further formulated with either the oxidizing agent or the reducing agent employed. If the cosmetic preparation is essentially oxidizing in nature, it will preferably be combined with oxidizing agent. The reverse situation is also applicable and in most cases, the cosmetic will have the ingredients thereof packed together with the reductant and catalyst, with the oxidant being separately packaged, usually in a different compartment of the dispenser. If some of the constituents of the cosmetic are oxidizing and others are reducing in nature, the composition may be formulated by such parts and one part may accompany the heat-generating oxidant and the other may be stored with the reductant. The main consideration is that no unwanted oxidation-reduction should occur due to premature combination of a heat-generating chemical of this invention with a cosmetic ingredient or other exothermic reactant. Of course, if so desired, the oxidizing agent and the thiooxypyrimidine may be kept separate and not formulated with any other cosmetic component. In such situations, the cosmetic may be separately dispensed from a container and only brought into contact with the heat-generating chemicals upon discharge from the container. In such an arrangement, a three compartment container may be employed or three or other number of separate containers may be used in conjunction.

Self-heating cosmetic preparations of this invention include various compositions intended for application topically to the human body. Usually these are applied to the skin or hair. They include face creams, body lotions, depilatories, tanning agents, antiperspirants, sun-screens, personal deodorants, hair creams, hair lotions, hair gels, shampoos, dyes, bleaches, rinses, shaving creams, makeup preparations, bath oils, facial treatments, astringents, after-shave lotions and many other related preparations. In most of these cosmetics, surface active materials or solubilizers are important or useful constituents, either as wetting agents, emulsifiers, or solvent aids. By the method of the present invention, utilizing starting materials that may be oxidized to such compounds, surface active materials may be self-heated. Such compounds are immediately solubilized or dispersed in the cosmetic, partly due to the heat generated in the exothermic reaction which produced them and partly due to their nature. The heat generated produces small currents in the cosmetic being dispensed and these currents will help to distribute surface active or solubilizing materials, including products of the thermogenic reaction, and by distributing such materials throughout the composition the ease of wetting of various portions of the cosmetic preparation and of solubilizing constituents thereof is further increased. Heat generated also may help to solubilize the cosmetic preparation ingredients and thereby improve homogeneity of the product. Such coaction between surface active agent or solubilizing material, which may be produced by the thermogenic reaction, the heat generated and the other cosmetic preparation ingredients is a useful result of the present invention and helps to avoid poorly dispersed ingredients or products of the exothermic reaction. The surface activity of a thermogenic product made also may help to distribute throughout the cosmetic the water and other byproducts of the heating reaction and thereby effects a better and more even heating of the cosmetic. Thus, pockets of undispersed materials in the cosmetic are avoided and the final product is more uniform.

The use of the present reductant-oxidant system for generating heat in cosmetic preparations being dispensed allows the employment of relatively small quantities of reductant to generate sufficient heat to raise the temperature of the cosmetic appreciably. Of course, as the molecular weight of the reductant becomes greater, if the heat of reaction does not increase proportionately, more reductant will have to be used. Nevertheless, the heat developed with the present compounds is sufficient to warm cosmetics satisfactorily, even with higher molecular weight thiooxypyrimidines. It is noted from a review of the specification and the examples which follow that it is preferred to employ approximately stoichiometric quantities of oxidizing agent and thiooxypyrimidine to produce the corresponding dioxypyrimidine and accompanying sulfate. It appears that a significant amount of heat is developed from intermediate reactions to produce the sulfoxide or sulfone and in some circumstances it might be desirable to stop the reaction at such stage. However, usually it is desirable to carry the reaction more to completion. Four moles of hydrogen peroxide will be sufficient to convert the thiooxypyrimidine to the corresponding dioxypyrimidine, with the sulfur being converted to a sulfate. Thus, in a usual alkaline medium, a sulfate, such as an alkali metal sulfate will be produced, not sulfuric acid. If the 6-carbon of the thiooxypyrimidine is also oxidized so that the corresponding oxy group is present thereon, rather than hydrogen, five moles of hydrogen peroxide will be employed. If, in addition, the 5-carbon thereof is similarly oxidized, seven moles of peroxide will be utilized. Following such oxidations, it may be possible to open the ring of the oxypyrimidine or otherwise fragment this compound, by further oxidation, either to the oxy or hydroxy derivative, utilizing additional hydrogen peroxide and generating more heat. Yet, such greater extent of oxidation is not accompanied by the expected development of extremely malodorous by-products, which is an important advantage of the present invention. Such an advantage is significant when it is kept in mind that some of the compounds previously suggested for use as reductants in heat-generating reactions, have been found to produce malodorous products. See U.S. Pat. No. 3,341,418, wherein thiourea is said to be oxidized under some circumstances to an undesirable and malodorous product.

Although there may be some structural resemblances of the present products to those described in the prior art, such as the thioureas and barbiturates of U.S. Pat. No. 3,341,418, the structural differences are considered to be unobvious and important, leading to the desired results obtained in accordance with the present invention. Thus, the thiobarbituric acids of U.S. Pat. No. 3,341,418 are not oxidizable to the same extent as the present compounds, differ significantly structurally from them and are not considered to be capable of generating as much heat per mole or per unit weight.

The following examples are given to illustrate but not to limit the invention. Unless otherwise indicated, all parts are by weight and all temperatures are in ° F.

EXAMPLE 1

|  | Parts |
| --- | --- |
| 2-Thio-4-oxypyrimidine | 5.0 |
| Sodium tungstate, aqueous solution (10% active ingredient) | 5.5 |
| Stearic acid | 8.3 |
| Distilled coconut oil fatty acids | 1.2 |
| Polyoxyethylene sorbitan monostearate (Tween 60) | 1.0 |
| Polyoxyethylene sorbitan stearate (Tween 61) | 1.0 |
| Cetyl alcohol | 1.5 |
| Lauric-myristic diethanolamide | 0.5 |
| Aqueous potassium hydroxide (34.2% KOH) | 3.8 |
| Sodium hydroxide (19.1% $Na_2O$) | 1.1 |
| Perfume | 0.8 |
| Water (deionized) | 70.3 |

The above composition is prepared by dissolving the 2-thio-4-oxypyrimidine in a small proportion of water, with the aid of some of the potassium hydroxide and sodium hydroxide solution, after which such solution and the balance of the caustic material are admixed with the rest of the composition at a temperature of about 100° F. Such addition is made slowly, over a period of about three minutes. The balance of the composition had previously been formulated by mixing together and blending at a temperature of about 185°-190° F. In preferred mixing methods, the fattier portion of the composition, including a stearic acid, coconut oil fatty acid and cetyl alcohol, are pre-blended and heated to about 185° F., at which temperature this mixture is added to the other constituents, including water, lauric-myristic diethanolamide, Tween 60 and Tween 61. Perfume is added last, after cooling.

Into a 6 ounce, two-compartment co-dispensing container, having a larger compartment and the smaller contained sac, both of which are arranged to dispense contents through a dispensing valve by means of a pressurized gas when such valve is actuated, into the larger compartment there are fed 144 grams of the above-described composition. 36 Grams of a 25% aqueous hydrogen peroxide solution are filled into the separate sac dispensing compartment or zone and the can is sealed, after which, it is pressurized through the valve by the addition of about 5.5 g. of an 87:13 isobutane:propane propellant mixture, producing a dispensing pressure of about 40 lbs./sq. in.

To use the shaving cream, it is only necessary to open the discharge valve, preferably after vigorously shaking the dispenser. The peroxide and cosmetic composition containing the specifically described reductants are metered from the valve together and react exothermically to heat the cosmetic to a temperature of about 140° F. When applied to the face, which is preferably previously washed with soap and water and left wet, the shaving cream gives a pleasant sensation of heat and shaving is easier, with the razor stroke appearing to be smoother and less irritating than when an unheated control composition of exactly the same formula, absent hydrogen peroxide, is employed.

When the formula is varied, with the catalyst being changed to ammonium molybdate, the same heating effect is noted. When catalyst is omitted, heating occurs but is much slower.

To improve the mildness of the self-heating shaving preparation, the mixed stearic acid and coconut oil, sodium and potassium soaps are 75% replaced by triethanolamine soaps, made by the addition of 90% active ingredient triethanolamine to the formula in place of some of the alkali metal hydroxide solutions. The product resulting is satisfactory, heats well and is considered to be milder to the skin than that previously described.

When, instead of employing 2-thio-4-oxypyrimidine, derivatives thereof are substituted, e.g., 1-methyl-2-thio-4-oxypyrimidine; 1-phenyl-2-thio-4-oxypyrimidine; 1-(5-hydroxyethyl)-2-thio-4-oxypyrimidine; 2-thio-6-methyl-4-oxypyrimidine; 2-thio-6-dipropoxy-4-oxypyrimidine or corresponding thiohydantoins, good stability is obtainable and the shaving creams or other cosmetics are raised to temperatures of 100° to 150° F., on dispensing. Such is also the case when variations are made in the proportions of the various constituents, within the ranges described in the specification and when, instead of shaving creams, other cosmetics are dispensed.

When 60 to 100% of the soaps are omitted from the present formula it is useful as a facial conditioner or hand cream composition. Similarly, when the fatty materials are omitted and preferably, when the detergent content is increased by the addition of 5% of sodium lauryl sulfate, a shampoo is produced. Intermediate compositions comprise hand creams, skin softening agents, superfatted detergents, shampoos, etc. In other variations, 10% of sodium thioglycolate or potassium thioglycolate are added to produce depilatory effects. In all such cases, the product is improved in its properties by being exothermically heated as it is dispensed.

EXAMPLE 2

|  | Parts |
| --- | --- |
| Thiohydantoin | 5.0 |
| Ammonium molybdate, aqueous solution (10% active ingredient) | 5.0 |
| Stearic acid | 8.6 |
| Distilled coconut oil fatty acids | 1.2 |
| Sorbitol (70% aqueous solution) | 5.0 |
| Tween 60 (polyoxyethylene sorbitan stearate) | 1.0 |
| Tween 61 (polyoxyethylene sorbitan stearate) | 1.0 |
| Cetyl alcohol | 0.5 |
| Lauric-myristic diethanolamide | 1.5 |
| Aqueous potassium hydroxide (34.2% KOH) | 3.8 |
| Aqueous sodium hydroxide (19.1% $Na_2O$) | 1.1 |
| Sodium silicate (N-silicate) | 1.5 |

EXAMPLE 2-continued

| | Parts |
|---|---|
| Perfume | 0.8 |
| Water, deionized | 64.0 |

A self-heating shaving cream of the above formula is prepared in the manner described in Example 1, with the N-silicate being added together with the caustic materials and the sorbitol being added with the Tweens. The composition is filled into a dispensing container of the same type described in Example 1, together with the same types and quantities of oxidant and propellant, and is used in a similar manner. In use, it too gives a more pleasant shave than an unheated control product. The temperature of application of the shave is also about 140° F. and the maximum temperature is developed within about eleven seconds after dispensing, as is the case with the product of Example 1.

When the amount of catalyst present is changed, so as to be diminished to about half its concentration, the development of heat is slowed and it takes about 15 seconds to reach the 140° F. maximum. When the catalyst is changed to sodium tungstate, at the same concentration as used for the molybdate, heat development is about the same. Product pH's are about 8.5–10.

In a similar fashion when the sodium soaps are replaced with triethanolamine soaps of the same types, good cosmetic foams are produced and they are less irritating to sensitive skins than the creams based on alkali metal soaps.

When, instead of utilizing thiohydantoin as the reductant, there is substituted for it a derivative thereof, e.g., 1-methyl-thiohydantoin; 1-hydroxyethyl-thiohydantoin; 1-acetyl-thiohydantoin; or 1-hydroxyethyl-5-phenyl-thiohydantoin, in the same quantity, essentially the same heat development results and the product made is as good a cosmetic or shaving foam. Similarly, when per-compounds, such as sodium perborate, potassium persulfate and ammonium percarbonate are substituted for some of the hydrogen peroxide, e.g., for from 5 to 50% of it, or replace it entirely, in some cases, good heating is also the result and the product resulting is a useful shaving cream or other cosmetic.

When the propellant is changed to a 0: 0 mixture of halohydrocarbon such as Freons 12 and 114, as good stability is obtainable and the character of the foam is not changed significantly. When the proportion of propellant is increased so that eight grams are utilized, the foam produced is puffier and dispensing is faster whereas when the amount is diminished to three grams per dispenser, the opposite effect obtains.

EXAMPLES 3–5 (Stock Formula)

| | Parts |
|---|---|
| Stearic acid | 7.2 |
| Distilled coconut oil fatty acids | 1.0 |
| Lauric-myristic diethanolamide | 1.0 |
| Glycerol | 5.0 |
| Potassium hydroxide, aqueous solution (34.2%) | 3.4 |
| Sodium hydroxide (19.1% Na$_2$O) | 1.0 |
| Perfume | 0.8 |
| Water | 50.7 |

The oil soluble components of the above composition, except perfume, are blended together at an elevated temperature, 185° F., and are cooled to 100° F., at which temperature the aqueous solution of alkalis is admixed and reaction with stearic acid is effected. After cooling the resulting heated product to about 75° F., perfume is added. This material is used as a cosmetic or shaving cream stock and is subsequently blended with reducing agent, catalyst, triethanolamine soap and additional water and is filled into dispensers such as those previously described, together with propellant and separately encased oxidant. The following are the formulas employed.

EXAMPLE 3

| | Parts |
|---|---|
| Stock (see above) | 106.2 |
| 2-Thio-4-oxypyrimidine | 4.6 |
| Sodium tungstate, 11.25% aqueous solution (90% pure) | 5.5 |
| Triethanolamine (90% active) or Potassium hydroxide (34.2%) | 12.0 |
| Water | 7.2 |
| Propellant, 85:15 isobutane:propane | 5.5 |
| Hydrogen peroxide, 15% aqueous solution | 36.0 |

The product is packed and employed in the manner previously described in Example 1. The shaving cream dispensed is at a temperature of 145°–150° F. after about 7–10 seconds and is of satisfactory shaving properties. The foam is stable, comfortable and softens the beard excellently. Essentially the same results are obtained when thiohydantoin is substituted for the reductant.

EXAMPLE 4

| | Parts |
|---|---|
| Stock (see above) | 110 |
| 2-Thio-4-oxypyrimidine | 1.9 |
| Sodium tungstate, 11.25% aqueous solution (90% pure) | 7.2 |
| Triethanolamine (90% active) | 2.5 |
| Potassium hydroxide (34.2%) | 2.5 |
| Water | 7.6 |
| Propellant, 85:15 isobutane:propane | 5.5 |
| Hydrogen peroxide, 10% aqueous solution | 36.0 |

In the above examples it is seen that the amounts of triethanolamine and alkali metal hydroxide are variable, with the total of such alkalis normally being sufficient to neutralize the tautomeric hydroxyl and sulfhydryl groups, or in slight excess. Additionally, of course, sufficient alkali is utilized to neutralize the fatty acid employed and convert it to suitable soaps.

EXAMPLE 5

| | Parts |
|---|---|
| Stock (see above) | 115.2 |
| 2-Thio-4-oxypyrimidine | 1.9 |
| Ammonium molybdate dihydrate (10% active) | 0.8 |
| Triethanolamine (90% active) | 15.0 |
| Potassium hydroxide (34.2%) | 2.8 |
| Water | 9.3 |
| Propellant 85:15 isobutane-propane | 5.5 |
| Hydrogen peroxide, 10% aqueous solution | 36.0 |

The compositions of Examples 4 and 5, prepared in the same manner as previously described, are dispensed as satisfactory self-heating shaving creams. The maximum temperature of such shaving creams is 110°–120° F. and is reached within about 10 seconds. When thiohydantoin is substituted for the 2-thio-4-oxypyrimidine of these examples, approximately the same temperatures are reached in the same periods of time after dispensing.

The present compositions, including those of the previously recited examples, and the reductants present are comparatively non-corrosive with respect to ordinary materials of construction of dispensing containers, including tinplate, resin-coated steel and plastic materials normally employed. Thus, blocking of valve parts is not encountered due to corrosion byproducts being released in the cosmetic being dispensed through the valve. Additionally, the present oxidants and reductants are compatible, as used, with normal cosmetic ingredients and do not form undesirable products that would adversely affect the cosmetic properties of these preparations. The products of the exothermic reaction are not gaseous and are readily soluble or dispersible in the cosmetics. By the use of known propellants, liquefied gases or pressurized gases, the products may be dispensed as liquids, emulsions, creams, foams or sprays, as desired. In foam preparations, the thermogenic reactants do not change the foaming activity of the liquefied gases or other foaming agents by introducing another gaseous byproduct. Thus, the desired foaming can be planned on the basis of the specific foaming agent being used and is not affected or modified by the generation of a gaseous byproduct of the thermogenic reaction. It follows then that the usual proportions of foaming agents or spraying propellants may be used with the present compositions, to dispense them in desired form. Of course, the normal expansion of a foam on heating does increase foam generation to a certain limited extent and in this respect can help to save propellant.

The lack of gas production in the reactions of this invention constitutes a protective feature because accidental rupturing of a sac containing a reactant, leading to contact of it with the other reactant of the thermogenic reaction, will not result in the generation of a gas. If it did, the pressure created might cause the container to explode. However, it has been found that the present exothermic reaction even if initiated in a closed container will not cause such an explosion.

The products of the oxidation-reduction reaction and the reactants themselves are of low toxicity, which is important, especially in products intended for contact with the human skin. Furthermore, they are also of acceptable odor, making them aesthetically desirable.

What is claimed is:

1. A dispensing apparatus or article for a self-heating cosmetic comprising constituents of a cosmetic composition stored in separate zones, in one of which there is present a compound which acts as a reductant, said compound having the formula:

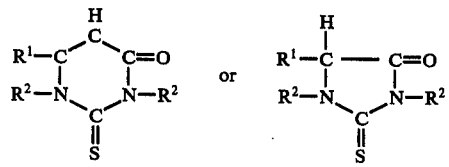

wherein $R^1$ is hydrogen, lower alkyl, phenyl, lower hydroxyalkyl, lower alkoxy, poly-lower alkoxy having 2 to 10 alkoxy groups, lower alkoxy-lower alkyl, poly-lower alkoxy-lower alkyl having 2 to 10 alkoxy groups, or lower alkanoyloxy and $R^2$ is hydrogen, lower alkyl, phenyl, lower hydroxyalkyl, lower alkoxy-lower alkyl, poly-lower alkoxy-lower alkyl having 2 to 10 alkoxy groups or lower alkanoyl, and in the other of which there is present an oxidizing agent exothermically reactive with the reductant to generate heat and heat the cosmetic when it is dispensed, and means for dispensing contents from both zones so that they are brought into contact with each other and with cosmetic ingredients of the cosmetic to produce a heated cosmetic, said reductant and oxidizing agent being employed in amounts relative to each other which range from stoichiometric proportions up to 50% in excess thereof of either said reductant or oxidizing agent.

2. A self-heated cosmetic preparation produced by the method of claim 1.

3. A dispenser according to claim 1 wherein there is present in the same zone as the reductant sodium tungstate or ammonium molybdate as catalyst for the oxidation-reduction reaction, in an effective proportion and amount to accelerate the exothermic reaction and heat the cosmetic to a temperature of at least 100° F. within 30 seconds after dispensing.

4. A dispenser according to claim 3 wherein the organic reductant is a thiooxypyrimidine.

5. A dispenser according to claim 4 wherein the reductant is 2-thio-4-oxypyrimidine.

6. A dispenser according to claim 5 wherein the oxidizing agent is a per-compound selected from the group consisting of hydrogen peroxide, sodium perborate, ammonium and potassium percarbonate, sodium and potassium persulfate, and sodium and urea peroxide.

7. A dispenser according to claim 6 wherein the per-compound is hydrogen peroxide, in aqueous solution.

8. A dispenser of self-heating shaving cream components comprising constituents stored in separate zones, in one of which there is present a reductant selected from the group consisting of thiooxypyrimidine and thiohydantoin, with higher fatty acid soap and water, and in the other of which there is present a per-compound oxidant, exothermically reactive with the reductant to generate heat and heat the shaving cream when it is dispensed, and means for dispensing contents from both zones so that they are brought into contact with each other and with constituents of the shaving cream preparation, to produce a heated shaving cream, said reductant and said oxidant being employed in amounts relative to each other which range from stoichiometric proportions up to 50% in excess thereof of either said reductant or oxidant.

9. A dispenser according to claim 8 wherein the reductant has one of the formulae of claim 1, the higher fatty acid soap is an alkanolamine soap of fatty acids in which a major proportion of the fatty acid content is of 16 to 18 carbon atoms per molecule, the per-compound is hydrogen peroxide in aqueous solution, and the means for dispensing the contents of the zones is a liquefied normally gaseous propellant.

10. A dispenser according to claim 9 wherein the reductant component comprises from 0.5 to 40% of the composition in the reductant zone, with triethanolamine soap, nonionic surface active agent and 0.2 to 2% of a catalyst for the redox reaction also being contained therein, and the oxidant component is an aqueous solution of hydrogen peroxide in which the active hydrogen peroxide content is from 4 to 25% of the weight of the reductant component.

11. A dispenser according to claim 10 wherein the shaving cream dispensed is propelled by a mixture of propane and isobutane, is exothermically heated to a temperature of at least 130° F., and comprises 50 to 85% water, 1 to 35% surface active agent, 5 to 20% soap and less than 25% adjuvants, and the nonionic surface active agent includes higher alkyl phenyl poly-lower alkoxy lower alkanol, with the pH at dispensing being from 7 to 10.

12. A dispenser according to claim 11 wherein the reductant is 2-thio-4-oxypyrimidine.

13. A dispenser according to claim 12 wherein there are present thioethanolamine stearate, nonyl phenyl polyoxyethylene ethanol of 30 oxyethylene groups per mole, lauric myristic diethanolamide, sodium tungstate or ammonium molybdate catalyst, 2-thio-4-oxypyrimidine, hydrogen peroxide and water.

14. A method of making a heated cosmetic preparation which comprises reacting a reductant selected from the group consisting of thiooxypyrimidines and thiohydantoins with a per compound as defined in claim 6 as an oxidizing agent which is exothermically reactive with the reductant in the presence of other ingredients of a cosmetic composition, so as to generate heat and produce such cosmetic in a heated state, said reductant and said oxidizing agent being employed in amounts relative to each other which range from stoichiometric proportions up to 50% in excess thereof of either said reductant or oxidizing agent.

15. A method according to claim 14 wherein the cosmetic is a shaving cream, the reductant is thiooxypyrimidine dissolved in liquefied propellant gas and with other shaving cream constituents, and the oxidizing agent is aqueous hydrogen peroxide.

* * * * *